United States Patent [19]
Bader et al.

[11] 3,944,591
[45] Mar. 16, 1976

[54] ENOLIC ETHERS OF ADIPIC DIALDEHYDE AND METHOD FOR PREPARING THE SAME

[76] Inventors: Andre Bader, 65 rue Henri Barbusse; Francis Weiss, 3 chemin du Perron, both of (69) Pierre Benite, France

[22] Filed: Jan. 23, 1973

[21] Appl. No.: 326,137

Related U.S. Application Data

[63] Continuation of Ser. No. 711,842, March 11, 1968, abandoned, which is a continuation-in-part of Ser. No. 702,524, Feb. 2, 1968, Pat. No. 3,787,484.

[52] U.S. Cl. ...... 260/465 F; 260/465.6; 260/473 R; 260/521 B; 260/602; 260/611 A; 260/613 R; 260/615 R
[51] Int. Cl.$^2$ ......... C07C 121/66; C07C 121/34; C07C 47/26; C07C 43/14
[58] Field of Search ........ 260/613 R, 615 R, 473 R, 260/521 B, 611 A, 465.6, 465 F, 602

[56] References Cited
FOREIGN PATENTS OR APPLICATIONS
1,205,618   9/1970   United Kingdom ................. 260/613

OTHER PUBLICATIONS

Berson et al., "J.A.C.S.," Vol. 86, pp. 5019–5020 (1964).

Viola et al., "J.A.C.S.," Vol. 87, pp. 1150 & 1151 (1965).

Chuche et al., C. R. Acad. Sci., Paris, Tome 262, pp. 567–570 (1966).

*Primary Examiner*—Richard J. Gallagher
*Assistant Examiner*—D. B. Springer

[57]   ABSTRACT

Enolic monoether and diether of adipic dialdehyde such as 6-methoxy-5-hexene-1-al, 1,6-dimethoxy-1,5-hexadiene, 1,6-bis-(2 hydroxy propoxy)-1,5-hexadiene are prepared by heating to a sufficiently high temperature for a Cope rearrangement, e.g., 150° to 450° C. of the corresponding monoether or diether of 1,5-hexadiene-3,4-diol.

4 Claims, No Drawings

ENOLIC ETHERS OF ADIPIC DIALDEHYDE AND METHOD FOR PREPARING THE SAME

CROSS REFERENCE TO RELATED APPLICATION

This application is a continuation of U.S. Pat. application Ser. No. 711,842, filed Mar. 11, 1968, now abandoned, which is in turn a continuation-in-part of application, Ser. No. 702,524, filed Feb. 2, 1968, now U.S. Pat. No. 3,787,484.

BACKGROUND OF THE INVENTION

I. Field of the Invention

This invention relates to enolic monoether and diether of adipic dialdehyde and the method for preparing the same.

II. Description of the Prior Art

Cope rearrangement is a well known reaction for the rearrangement of 1,5-hexadienic compounds. In a special situation when the 1,5-hexadienic compound is substituted at the 3 or possibly the 4 position with a hydroxyl group, the normal Cope rearrangement is modified because the rearrangement product, which would be an enol, cannot exist alone and rearranges itself into a corresponding carboxylic derivative. The term "Oxy-Cope Rearrangement" has been proposed to describe this variant of the general reaction (see for example *J. Am. Chem. Soc.*, 1964, 86, pp. 5017–5018). In addition, it is known that when the rearrangement is carried out with a disecondary 1,5-hexadiene-3,4-diol, the normal product of Oxy-Cope rearrangement which would be an adipic dialdehyde, is not isolatable since it is cyclized immediately by internal crotonization into a cyclopentenic aldehyde (see for example *Ann. Chim.* 1934, 1,p. 55 C.R. Acad. Sc. Paris 1966, 262, page 567 - series C).

Such an evolution is not unexpected because the extraordinary instability of the adipic dialdehyde has long been recognized. The instability of the adipic dialdehyde is due to the easiness of its structure to cyclize by internal aldolization or crotonization, for example, even during simple heating of their aqueous solutions. This instability coupled with the fact that there exists no economic process for making these compounds offer an explanation why these products up to now have not been industrially developed despite their particularly reactive dialdehyde structure. In fact, it is known that the dialdehydes are extremely valuable products because of their many applications particularly in the fields of textile dressings, in the paper industry, for chemical synthesis, for the preparation of polyacetals, as well as their known application as disinfectants, as bactericides and others.

SUMMARY OF THE INVENTION

We have discovered that monoether and diether of adipic dialdehyde of the formulas

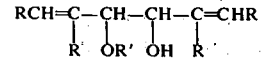

and

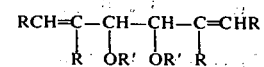

respectively, wherein each R is a hydrogen atom, an alkyl radical containing 1 to 4 carbon atoms, or a phenyl radical which *may* be inertly substituted and each R' is an alkyl radical containing 1 to 4 carbon atoms which may be substituted by one or more halogen, hydroxy or nitrile groups, when they are heated either alone or in the form of a mixture to a temperature sufficiently high for a Cope rearrangement, transform to their corresponding enolic monoether and diether of adipic aldehyde of the formulas

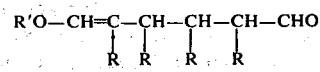

and

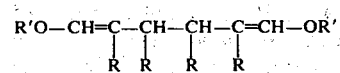

respectively.

DESCRIPTION OF THE PREFERRED EMBODIMENTS

Even though the starting materials for the process of this invention are disubstituted at the 3 and 4 positions, we found that the Cope rearrangement took place normally without further rearrangement or transformation to produce the enolic monoether or diether of the adipic dialdehyde

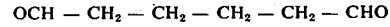

The rearrangement takes place with good yields and the products obtained are sufficiently stable to undergo the necessary isolation and purification treatments, as well as for long term storage. The present invention thus offers an efficient and economic method for the production of stable new derivatives of adipic aldehyde which have applications either alone by virtue of their own structure or as agents for the synthesis of adipic dialdehyde.

The starting materials, the carboxylic monoether and diether of 1,5-hexadiene-3,4-diol of the formulas

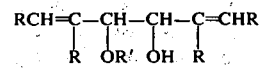

and

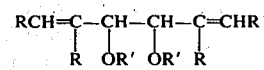

can be prepared readily by etherification of the corresponding 1,5-hexadiene-3,4-diol which in turn are obtained by reductive dimerization of unsaturated α,β aldehydes such as acrolein, methacrolein, crotonaldehyde and cinnamaldehyde and its ring substituted derivatives.

R of the starting materials is hydrogen or a hydrocarbon radical. Preferably the hydrocarbon radical is selected from the group consisting of alkyl and aryl radicals including such radicals when inertly substituted. When R is an alkyl, it typically may be a straight chain alkyl or a branched alkyl containing 1 to 4 carbon atoms including methyl, ethyl-n-propyl, i-propyl, n-butyl, t-butyl, and i-butyl. When R is an aryl, it may be phenyl which may be mono-, bi- or tri-substituted by groups including alkyl containing 1 to 4 carbon atoms; halogens notably, fluoro, chloro and bromo radicals; and hydroxy, methoxy, ethoxy, carboxy, carbomethoxy, carboethoxy and methylol radicals. R' of the starting material is an alkyl radical containing 1 to 4 carbon atoms which may be substituted by one or more halogen, hydroxy or nitrile groups.

Etherification of 1,5-hexadiene-3,4-diol may be carried out in the usual manner, such as by the action of methyl or ethyl sulfate or alkyl halides to prepare the saturated carboxylic monoether or diether of the diol, or by the action of alkylene oxide e.g. ethylene or propylene oxide to prepare the hydroxy alkylene ether of the diol, as described in French patent application Ser. No. 85,818, filed Dec., 1966 by the assignee of this application, or by cyanoethylation, e.g., by the action of acrylonitrile, to prepare the ether containing the nitrile group in R' radical.

The selectivity of the present reaction was heretofore unknown. It is known that ethers with allylic characteristics are thermally not very stable and are subject to almost quantitative pyrolytic transformation to form an olefinic chain by transferring a hydrogen atom from the saturated radical to the allylic radical and to derive an aldehyde or a ketone from the saturated radical. (See for example *J. Chem. Soc (b)*, 1966, p. 1245). A similar process involving the monoether and diether of adipic dialdehyde used as the starting material of the process of this invention, would lead to a conjugated 2,4-hexadiene, and one would fear that the conjugation is undesirable in this reaction.

The rearrangement reaction of the ethers of 1,5-hexadiene-1,6-diol is carried out by heating these materials either alone or in a mixture to a temperature between about 150° and 450° C. This operation can be carried out in the liquid phase, by heating the starting materials themselves, or their solution in an inert, thermally stable solvent, such as an aliphatic or an aromatic hydrocarbon or an ether, for example, diphenyl ether.

The Cope rearrangement can be carried out at atmospheric pressure and can be effected, for example, at the boiling temperature of the mixture, or else if necessary, the operation can be carried out in an autoclave or a sealed tube. The rearrangement can also be carried out under reduced pressure and it is possible, when the operation is carried out at the boiling point of the system, to distill off part or all of the mixture during the reaction.

It is advantageous to add a small amount of a polymerization inhibitor, such as hydroquinone, the monomethyl ether of hydroquinone, t-butylcatechol, p-phenylenediamine or a copper salt in the amount of 0.01 to 1%. The required heating time, which is variable according to the temperature used and the nature of the product used, is generally in the order of about 0.5 to 5 hours.

The Cope rearrangement can also be carried out in a gas phase, by passing the starting ether vapors, possibly diluted with an inert gas such as nitrogen, carbon dioxide, or argon, through an empty tube, or one filled with inert packing designed to homogenize the temperature in the reactor. Such a packing can be made up of glass or steel balls, ceramic rings, sand, etc. The packing can be in the form of a fixed bed, or in the form of a fluidized bed using the inert gas and vapors as fluidizing gas.

The residence time of the vapors in such a reactor can vary over wide limits; for example, the operation can be carried out with residence times between about 1 and 500 seconds.

The new compounds according to the invention can find numerous applications in various fields. In the first place, as has already been said, they can be used for synthesizing corresponding adipic dialdehyde since, like enolic ethers in general, they are easily hydrolized in a slightly acid medium. The compounds according to the invention can be utilized for example as agents for water disinfecting, in textiles, as bactericides, as reticulation and insolutilizing agents for proteins or for polyhydroxylated polymers, in textile dressings, in paper treatment, in the reticulation of polyvinyl alcohols, or other hydroxylated polymers, etc.

On the other hand, the unsaturated groups of the product of this invention can be put to use to carry out the reactions of polymerization or copolymerization with vinyl monomers such as vinyl acetate, vinyl ethers, acrylic and methacrylic nitriles or esters, styrene, the α-olefins, etc. To sum up, these are very interesting raw materials and are suitable for the synthesis of numerous bi- or polyfunctional compounds, such as the 1,6-hexanediols, 1,6-diamino hexane, etc.

The following non-limiting examples illustrate the preparation of several ethers according to the invention.

EXAMPLE I

Preparation of 6-methoxy-5-hexene-1-al

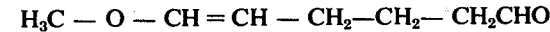
$H_3C — O — CH = CH — CH_2—CH_2— CH_2CHO$

As starting material there was used 4-methoxy-1,5-hexadiene-3-ol prepared by the action of methyl sulfate on 3,4-dihydroxy-1,5-hexadiene (divinylglycol), which had the following properties:

B.$P_{50}$ = 88° – 88.5°C.
$n_D^{20}$ = 1.450;
$d_4^{20}$ = 0.944

Gas chromatography analysis of this product shows that it was above about 95% pure (it contained about 1% of dimethylether.)

The Cope rearrangement was carried out in the vapor phase, in a reactor consisting of a stainless steel tube 2 cm. in diameter and 100 cm. in length, bent into a U-shape and furnished with glass balls 3 mm in diameter and filled up to 30 cm. The reactor was placed in an electric furnace and heated to 330° C. There was introduced into the reactor drop by drop under a stream of nitrogen at the rate of 10 liters/hour, measured under normal conditions, 15 grams per hour of 4-methoxy-1,5-hexadiene-3-ol which was vaporized immediately on contact with the glass balls. At the outlet of the reactor the mixture of vapors and nitrogen was cooled by a refrigerant, which condensed the greater part of the reaction products, then by a solid carbon dioxide refrigerant. The operation took 2 hours using 30 grams of raw material (0.15 mole).

There were collected 28.5 grams of pyrolysate, analysis of which gave the following results:
29% by weight of untransformed 4-methoxy-1,5-hexadiene-3-ol (i.e., 29% of the amount used);
1% by weight of untransformed 3,4-dimethoxy-1,5-hexadiene;
41% by weight of 6-methoxy-5-hexene-1-al;
4.0% by weight of 1,6-dimethoxy,5-hexadiene.

The yield was 58% of 6-methoxy-5-hexene-1-al. The product was isolated by fractional distillation which was a colorless liquid with the following properties:

$B.P._{25} = 92.5° - 94.5°C$;
$n_D^{20} = 1.448$; and
$d_4^{20} = 0.951$

It was a mixture of cis-trans isomers. The characteristic bands of the infrared spectrum of the product in (cm$^{-1}$) were as follows:

1725, 2725 (aldehyde group); 735, 930, 1655, 1665, 3010, 3050 (double bond); 1110, 2830 (CH$_3$O—).

The two isomers were identified by gaseous chromatography separation using a column of polyethyleneglycol. The cis isomer represents about two thirds of the mixture.

EXAMPLE II

Preparation of a Mixture of 6-methoxy-5-hexene-1-al and 1,6-dimethoxy-1,5-hexadiene, (the latter having the following formula:

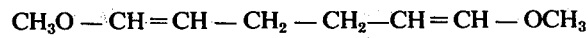

$CH_3O — CH = CH — CH_2 — CH_2 — CH = CH — OCH_3$

The starting material used for the Cope rearrangement was a mixture consisting of 83% by weight of 3,4-dimethoxy-1,5-hexadiene and 15.5% by weight of 4-methoxy-1,5-hexadiene-3-o1 prepared by reacting methyl sulfate with divinylglycol in the presence of sodium hydroxide. The characteristics of the starting material were as follows:

$B.P._{-50} = 73° - 78°C$;
$n_D^{20} = 1.435$; and
$d_4^{20} = 0.902$.

The rearrangement was carried out under the same conditions as set forth in Example I, (i.e. temperature 330° C., and 15 gm/hr. of starting material in 10 liter per hour of nitrogen carrier). After 2 hours of reaction in which 30 grams (0.211 mole) of starting material were used, the pryolysate collected was 27.9 grams, analysis of which gave the following results:

20% by weight of untransformed 3,4-dimethoxy-1,5-hexadiene (i.e. 0.039 mole);

3% by weight of 4-methoxy-1,5-hexadiene-3-o1 (i.e. 0.007 mole)

13.5% by weight of 6-methoxy-5-hexene-1-al (0.03 mole).

The amount of starting materials transformed was 0.211 − (0.39 + 0.007) = 0.165 mole; and the amount of rearranged product was 0.095 + 0.030 = 0.125. The rate of transformation in mass was 78% and the yield of the rearrangement was 75–76%.

Fractional distillation collected a mixture of 1,6-dimethyl-1,5-hexadiene (76.5% by weight) and 6-methyl-1,5-hexene-1-al (21.7% by weight). The product was colorless;

$B.P._{25} = 82° - 90°C$;
$n_D^{20} = 1.454$;
$d_4^{20} = 0.919$.

EXAMPLE III

Preparation of 1,6-bis(2-hydroxypropoxy)-1,5-hexadiene

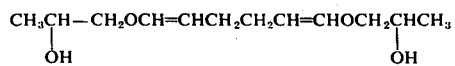

$$CH_3\underset{OH}{\underset{|}{CH}}—CH_2OCH=CHCH_2CH_2CH=CHOCH_2\underset{OH}{\underset{|}{CH}}CH_3$$

The starting material 3,4-bis(2-hydroxypropoxy)-1,5-hexadiene was prepared by adding 2 molecules of propylene oxide to one molecule of divinylglycol in accordance with the method described in French patent application mentioned previously.

The reactor described in the previous Examples was used for the Cope rearrangement. The temperature of the heating stage was 350° - 365° C. The nitrogen carrier used was at a rate of 10 liter per hour carrying 17.8 grams per hour of starting material to the reactor. There were collected 14.6 g. of pyrolysate of which 37% by weight was the non-transformed starting material, and 55% by weight was 1,6-bis(2-hydroxypropoxy)1,5-hexadiene.

The total transformation rate was 70% and the yield was 64% of the theory.

Fractional distillation produced 7.3 grams of a thick product which was a colorless liquid $B.P._{-0.5} = 120° - 125°C$;
$n_D^{20} = 1.477$;
$d_4^{20} = 1.047$.

Infrared spectrum analysis showed the presence of cis and trans double bonds, and gas chromatography separated the two isomers. The frequency characteristics of the IR spectrum (in cm$^{-1}$) was as follows:

735, 925, 1655, 1670; 3045 (double bonds), 1100 (ether); and 3520, 3620 (OH).

EXAMPLE IV

Preparation of 1,6-bis(2-cyanoethoxy)-1,5-hexadiene:

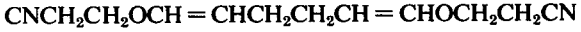

$CNCH_2CH_2OCH = CHCH_2CH_2CH = CHOCH_2CH_2CN$

The starting material used was 3,4-bis(2-cyanoethoxy)-1,5-hexadiene prepared by cyanoethylation of divinylglycol which had the following characteristics:

$B.P._{-0.5} = 135° - 140°C$;
$n_D^{20} = 1.468$;
$d_4^{20} = 1.026$.

The Cope rearrangement was carried out in a reactor as described using a temperature in the range of 350° - 360° C while introducing the 50 grams of starting material thereinto for a period of 3 hours using a current of nitrogen equal to 10 liters per hour. The pyrolysate collected weighed 47.5 grams of which 66% was the product and 13% was the non-transformed material. The rate of transformation was 87% and the yield of 1,6-bis-(2-cyanoethoxy)-1,5-hexadiene based on the initial material consumed was 71%.

Fractional distillation produced 29.4 grams of 1,6-bis(2-cyanoethoxy)-1,5-hexadiene in the form of a colorless liquid.

$B.P._{-0.5} = 152° - 155°C$;
$n_D^{20} = 1.474$;
$d_4^{20} = 1.035$.

Infrared spectrum analysis presented the following band characteristics (in cm$^{-1}$):

740, 930, 1660, 1670, 3050, 3075 (slope cis and trans double donds); and 2220, 2260 (CN)

A weak IR band at 1725 cm$^{-1}$ indicated the presence of impure aldehyde.

We claim:

1. A method for preparing enolic monoether or diether of adipic dialdehyde which method comprises the step of heating to a temperature between about 150° and 450° C and in the presence of an inert and thermally stable solvent for a Cope rearrangement a monoether or diether of the formulas

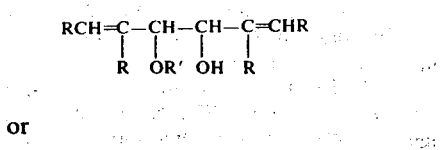

or

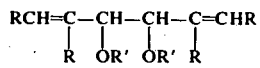

respectively, wherein each R is a hydrogen atom, an alkyl of 1 to 4 carbon atoms, phenyl, or phenyl having substituted therein an alkyl of 1 to 4 carbon atoms, a halogen, hydroxyl, methoxy, ethoxy, carboxy, carbomethoxy, carboethoxy, or methylol substituent, and each R' is an alkyl of 1 to 4 carbon atoms or a halogen, hydroxy, or cyano mono-substituted alkyl of 1 to 4 carbon atoms, and recovering the corresponding enolic monoether or diether of adipic aldehyde of the formulas

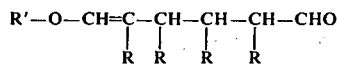

or

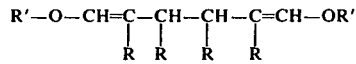

respectively.

2. A method according to claim 1 wherein the Cope transformation is carried out in the presence of a polymerization inhibitor.

3. A method for preparing enolic monoether or diether of adipic dialdehyde which method comprises the step of heating to a temperature between about 150° and 450° C and in the vapor phase for a Cope rearrangement a monoether or diether of the formulas

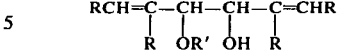

or

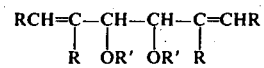

respectively, wherein each R is a hydrogen atom, an alkyl radical of 1 to 4 carbon atoms, phenyl, or phenyl having substituted therein an alkyl of 1 to 4 carbon atoms, a halogen, hydroxyl, methoxy, ethoxy, carboxy, carbomethoxy, carbomethoxy, carboethoxy, or methylol substituent; and each R' is an alkyl of 1 to 4 carbon atoms or a halogen, hydroxy, or cyano monosubstituted alkyl of 1 to 4 carbon atoms, and recovering the corresponding enolic monoether of diether of adipic aldehyde of the formulas

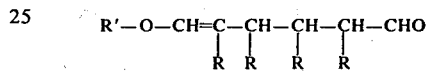

or

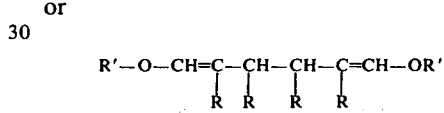

respectively.

4. A method according to claim 3 wherein the Cope rearrangement is carried out in the presence of an inert gas.

* * * * *

UNITED STATES PATENT AND TRADEMARK OFFICE
CERTIFICATE OF CORRECTION

PATENT NO. : 3,944,591
DATED : March 16, 1976
INVENTOR(S) : ANDRE BADER ET AL.

It is certified that error appears in the above-identified patent and that said Letters Patent are hereby corrected as shown below:

Page 1, below the "Inventors", insert the following:

-- Assignee: Produits Chimiques Ugine Kuhlmann --.

Column 4, lines 35, 54, and 64; and Column 5, lines 26 and 42, "-ol" should read -- -ol--.

Column 6, line 59, "donds" should read -- bonds --.

Signed and Sealed this fifteenth Day of June 1976

[SEAL]

Attest:

RUTH C. MASON
Attesting Officer

C. MARSHALL DANN
Commissioner of Patents and Trademarks